United States Patent
Bhaskaran et al.

(10) Patent No.: US 7,261,769 B2
(45) Date of Patent: Aug. 28, 2007

(54) **STABILIZED ANTHOCYANIN EXTRACT FROM *GARCINIA INDICA***

(75) Inventors: Sunil Bhaskaran, Wanorie (IN); Sevanti Mehta, Houston, TX (US)

(73) Assignee: Unibar Corporation, Houston, TX (US)

( * ) Notice: Subject to any disclaimer, the term of this patent is extended or adjusted under 35 U.S.C. 154(b) by 0 days.

(21) Appl. No.: 10/563,050

(22) PCT Filed: Jul. 1, 2004

(86) PCT No.: PCT/US2004/021305

§ 371 (c)(1), (2), (4) Date: May 1, 2006

(87) PCT Pub. No.: WO2005/007088

PCT Pub. Date: Jan. 27, 2005

(65) Prior Publication Data

US 2006/0230983 A1    Oct. 19, 2006

Related U.S. Application Data

(60) Provisional application No. 60/484,781, filed on Jul. 3, 2003.

(51) Int. Cl.
| | |
|---|---|
| *A61K 36/00* | (2006.01) |
| *A01N 65/00* | (2006.01) |
| *C07D 311/00* | (2006.01) |
| *C09B 61/00* | (2006.01) |
| *C09B 67/00* | (2006.01) |

(52) U.S. Cl. .............. 106/493; 106/498; 424/777; 426/250; 514/451; 514/460

(58) Field of Classification Search ............ 106/493, 106/498; 424/777; 426/250; 514/451, 460
See application file for complete search history.

(56) References Cited

U.S. PATENT DOCUMENTS

| | | | |
|---|---|---|---|
| 4,172,902 A | 10/1979 | Asen et al. | |
| 5,656,314 A | 8/1997 | Moffett et al. | |
| 5,783,603 A | 7/1998 | Majeed et al. | |
| 5,908,650 A | 6/1999 | Lenoble et al. | |
| 6,132,791 A | 10/2000 | Fox | |
| 6,147,228 A | 11/2000 | Ibnusaud et al. | |
| 6,160,172 A | 12/2000 | Balasubramanyam et al. | |
| 6,180,154 B1 | 1/2001 | Wrolstad et al. | |
| 6,207,714 B1 | 3/2001 | Clouatre et al. | |
| 6,221,901 B1 | 4/2001 | Shrivastava et al. | |
| 2003/0207942 A1 | 11/2003 | Bhaskaran et al. | |

FOREIGN PATENT DOCUMENTS

| | | |
|---|---|---|
| WO | WO9903464 | 1/1999 |
| WO | WO 0214477 | 2/2002 |

OTHER PUBLICATIONS

PCT International Search Report, PCT/US2004/021305 published Nov. 17, 2005, 1 p.

*Primary Examiner*—Anthony J. Green
(74) *Attorney, Agent, or Firm*—Conley Rose, P.C.

(57) ABSTRACT

A method of making a red pigmented composition is disclosed which includes (a) preparing an aqueous extract of *Garcinia indica* fruit comprising at least one red colorant; (b) treating the extract with a cation exchange resin so that one or more red colorant associates with the resin; (c) eluting the red colorant from the resin with an eluting solution containing one or more alcohol such as methanol, ethanol and isopropanol and one or more acid such as hydrochloric acid, citric acid, acetic acid, tartaric acid and hydroxy citric acid to yield a red-colored eluate; (d) collecting and concentrating the eluate to provide a concentrate; and (e) adding an antioxidant agent and/or placing the concentrate in an aseptic container in a non-oxidizing atmosphere. A combination comprising the resulting stabilized *Garcinia* extract in aseptic packaging in a non-oxidizing atmosphere is also disclosed, along with methods of use.

19 Claims, 2 Drawing Sheets

STABILIZED ANTHOCYANIN EXTRACT FROM *GARCINIA INDICA*

CROSS-REFERENCE TO RELATED APPLICATIONS

This application is a 371 of PCT International Application No. PCT/US04/21305 filed Jul. 1, 2004 which claims the benefit of U.S. Provisional Application No. 60/484,781 filed Jul. 3, 2003, the entire disclosures of which are herein incorporated by reference.

BACKGROUND OF THE INVENTION

1. Technical Field of the Invention

The present invention generally relates to plant-derived natural red pigment, and more particularly to anthocyanins from the fruit of *Garcinia indica*. Still more particularly, the present invention relates to methods of extracting and stabilizing this pigment, and its use as a colorant.

2. Description of Related Art

Natural red color or hues of red color are frequently employed for adjusting the color of various foodstuffs, beverages, pharmaceuticals and the like. Some of the conventional red colorants in use today are derived from insects, for example, cochineal. Other red colorants are synthetic in origin. As a result, many of the existing red colorants have distinct disadvantages with respect to suitability for use in foodstuffs and beverages meant for human consumption.

In recent times, a variety of natural sources of red colorants have been identified and methods for extraction of natural red pigments have been described. For example, a natural red color has been extracted from grape skin and is has been standardized with respect to specific color value and percentage of anthocyanin content. This grape-derived pigment has been stabilized for use in dairy, beverages, and confectionary. While this natural pigment is satisfactory for some purposes, the problem remains that it does not give the precise hues that are desired in some food and beverage products.

U.S. Pat. No. 4,172,902 (Asen et al.) describes a method for extracting an anthocyanin red color from the 'Heavenly Blue' morning glory flower. Although morning glories provide an excellent red pigment, the availability of this natural source is too limited for widespread or commercial use. Therefore, there are problems associated with making use of this anthocyanin pigment for coloring foodstuffs and beverages.

U.S. Pat. No. 5,908,650 (Lenoble et al.) describes certain anthocyanin-based colors that are stabilized with respect to loss of color due to pH, heat or light by water-soluble pigment-improving extracts of plant material such as rosemary, sage and peppermint. The active pigment-improving agent is said to be a flavonoid glycuronide or a flavonoid glucuronide.

U.S. Pat. No. 6,132,791 (Fox) describes the extraction of a natural red sunflower anthocyanin colorant that is said to have naturally stabilized color qualities. According to the procedure described in that patent, sunflower hulls are heated in an aqueous solution at pH 2-6. to produce a red juice that is heat and light stable over a pH range of about 1-6.

U.S. Pat. No. 6,180,154 (Wrolstad et al.) describes a natural colorant preparation from potato extract. However, the presence of steroidal glyco-alkaloids in potato introduces the potential for toxicity in red color extracts obtained from red potato. One way to address this problem is to develop a variety of red potato that is lower in the toxic glyco-alkaloid, and to use it for extraction of the red potato pigment.

Japanese Patent Nos. 223756 and 25460 describe studies in which red pigments were extracted from red cabbage and the extracts were evaluated for anthocyanin color values. Although accepted and proven methods for extraction of red color from red cabbage exist, even those methods have practical shortcomings, which preclude the cost effective application of such methods, especially for commercial applications. One such drawback is that methods, which employ alcohol extraction of the red pigment, can leave traces of the alcohol in the product. If alcohol remains in the extract, even in small amounts, it can adversely affect the filtration membrane used for concentration of the pigment extract. Another drawback is that when alkali is used for extraction of color pigments, stability of the pigment solution is badly affected, leading to degradation of the pigment by the alkali. Methods that use sulfuric acid or sulfate liquor for extraction of red coloring from red cabbage have as a shortcoming the generation of sulfur dioxide during heating. Sulfur dioxide production is highly undesirable for environmental safety reasons as well as because of its tendency to form foul smelling sulfur-containing compounds in the final product.

WO 02/14477 describes certain anthocyanin pigments isolated from the fruits of *Garcinia indica*.

While the demand for natural red pigment remains high, the existing colorants and their methods of preparation are not able to meet the existing demand. Even though some of the known sources are renewable, or can be grown in great quantity, the supply of satisfactory red colorants is not adequate for current demand. There is still an unmet need for practical red colorant compositions that are safe for human consumption, avoid discoloring or fading, and impart to foods and other products the desired hues.

BRIEF SUMMARY OF PREFERRED EMBODIMENTS

The compositions, combinations and methods of the present invention overcome many of the shortcomings associated with other red colorants. A method has been developed to extract the red color from the fruit of *Garcinia indica* and to prepare a natural red colorant for use in a wide variety of foodstuffs, beverages, nutraceuticals, pharmaceuticals, toiletries and the like, and as a natural anti-oxidant in such products.

Accordingly, in certain embodiments of the present invention a new process or method of extracting and stabilizing a red pigmented *Garcinia* extract is provided. In certain embodiments the process includes treating an aqueous extract of *Garcinia indica* fruit with a cation exchange resin such that at least one red colorant attaches or otherwise associates with the resin. The colorant is eluted from the resin using a solution containing an alcohol-acid mixture. In certain embodiments the alcohol is methanol, ethanol or isopropanol, and the acid is hydrochloric acid, or, preferably, an organic acid such as acetic, citric, hydroxy citric, or tartaric acid. In certain embodiments, the resin is washed with water before the red pigmented components are eluted from the resin. The resulting red-colored eluate is collected and concentrated. In some embodiments, one or more color-stabilizing agent or antioxidant, such as tocopherol, an aqueous extract of *Occimum sanctum*, and an aqueous extract of *Azadiracta indica*, is added to the composition. The term "color stabilizing" means that loss of color due to oxidation of color pigment molecules (for example, arising from exposure to oxidizing conditions of pH, light or heat) is deterred or prevented or reduced. In certain embodiments, the method includes placing the red pigmented *Garcinia* extract concentrate, with or without additional antioxidant, in aseptic packaging in an inert or non-oxidizing environment so as to preserve the product in a color-stabilized condition. In some embodiments the environment comprises a vacuum or a gas chosen from the group consisting of nitrogen and helium, preferably nitrogen.

In some embodiments the process includes concentrating the eluate by evaporating under vacuum, preferably in the range of 25-50 mm mercury, to yield a concentrate. In some embodiments the evaporation is carried out at a temperature below 40° C., preferably in the range of 20-35° C.

Also provided in accordance with certain embodiments of the present invention is a red pigmented composition comprising the *Garcinia* extract resulting from an above-described method.

In accordance with still other embodiments of the present invention, a combination is provided which comprises a red-pigmented extract of *Garcinia indica* comprising at least one anthocyanin compound, preferably cyanidin-3-glucoside and cyanidin-3-sambubioside. In certain preferred embodiments the red-pigmented extract comprises about 61 wt % cyanidin-3-glucoside and about 35 wt % cyanidin-3-sambubioside. The extract is contained in an aseptic, anti-oxidant atmosphere and is prepared in accordance with an above-described method. In some embodiments, the composition also includes a color stabilizing agent, as indicated above. In some embodiments the combination includes a concentrate, which may be thick or paste-like. In other embodiments the combination comprises an aqueous solution. In various embodiments the combination comprises a food coloring, food, beverage, nutraceutical, pharmaceutical or toiletry product.

In certain other embodiments of the present invention, methods of using the color-stabilized red pigmented *Garcinia* extract are provided which include tinting foods, beverages, nutraceuticals, pharmaceuticals, toiletries and the like, to impart a red color to the product. These and other embodiments, features and advantages of the present invention will become apparent with reference to the following description and drawings.

DETAILED DESCRIPTION OF PREFERRED EMBODIMENTS

Figure 1:
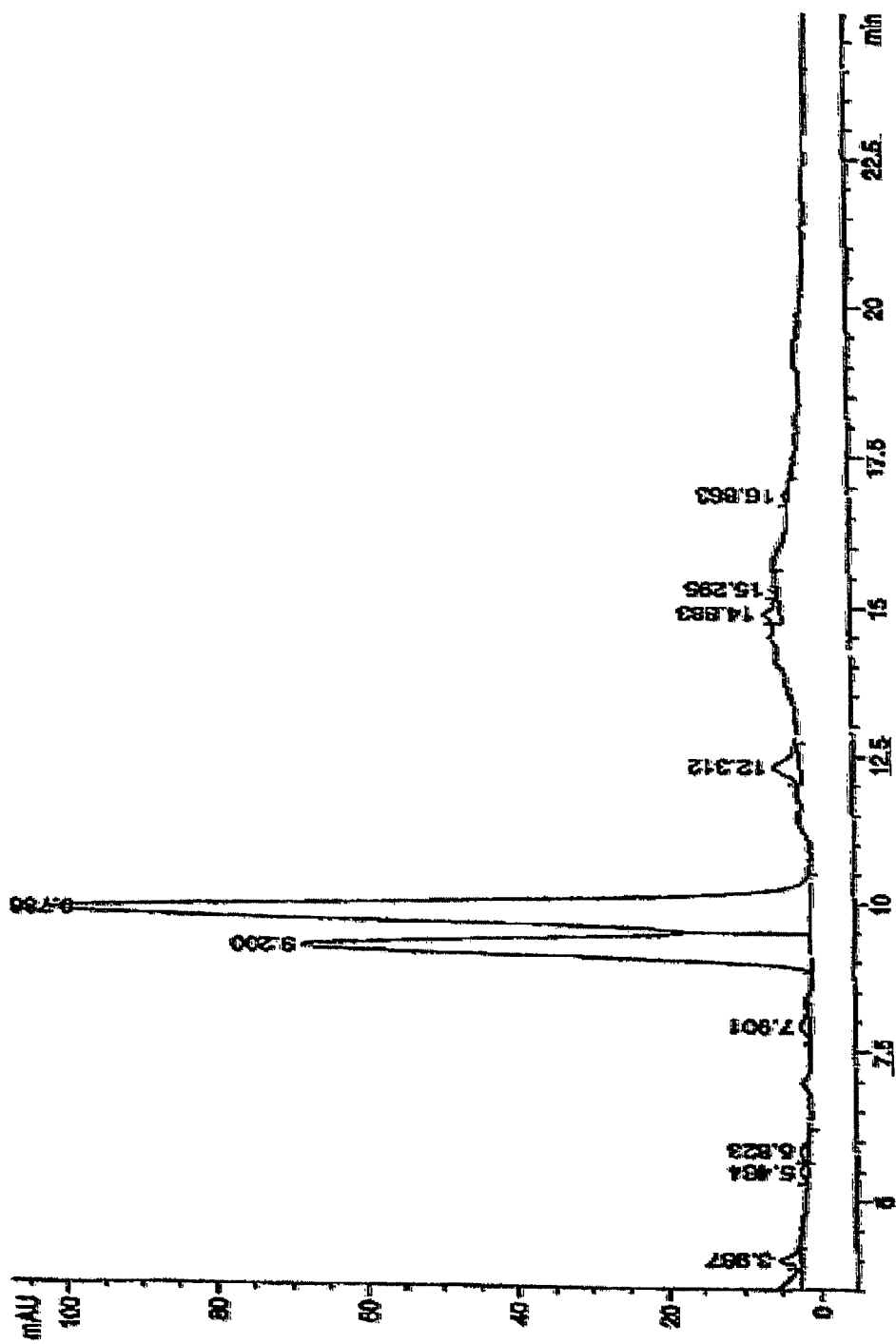
FIG. 1 is a HPLC chromatogram showing the anthocyanin profile of a representative sample of a red colorant prepared in accordance with one embodiment of the present invention

The well-known tropical fruit *Garcinia indica* is native to the Indian sub-continent, particularly at the Western Ghats, and widely used in South Indian and Konkan delicacies as a flavor and taste-imparting agent. It is also a rich source of natural anthocyanin red pigment. *Garcinia indica* is a perennial tree that yields an abundance of red fruits annually. It is a seasonal fruit that is generally available fresh only during the months of March to June. The fruit can be dried and preserved for a long period of time without loss of its red pigment. Typically the drying process includes de-hydrating either by shade drying in the sun or by applying controlled heat to a bed of fruits.

Anthocyanins are the best-known natural pigments. They are responsible for the orange, red, blue, violet and magenta colors in plants. These anthocyanins have high tinctorial values. Anthocyanins are polyphenols and are usually classified with the flavanoids group. These are red or orange colored pigments. The chemical structure of the anthocyanin comprises a multiring system with a positively charged hetero oxygen. The general structure of the anthocyanin nucleus can be represented as follows:

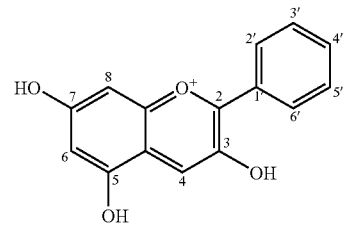

When the general structure is substituted as shown below, the name of the resulting compound is as indicated in parentheses.

a.) 4'=OH (pelarigonidin)
b.) 3', 4'=OH (cynidin)
c.) 3', 4', 5'=OH (delphinidin)
d.) 4'=OH, 3'=OMe (peonidin)
e.) 4', 5'=OH, 3'=OMe (peturidin)
f.) 4'=OH, 3', 5'=OMe (malvidin)

Preparation of Red Colorant from *Garcinia indica*

The procedure for preparing a red colorant from *Garcinia indica* generally includes the following: The red, fleshy fruit is crushed and passed through a pulper to express the fruit juice, which contains the anthocyanin red pigments. This juice is diluted with water so as to make it flowable. This liquid is then filtered through 5μ filter cloth fitted in a plate and frame filter press. This juice is used for extraction of anthocyanins as described in the following examples.

Alternatively, preparation of the extract may commence using dried fruit instead of fresh. In this case, the dried fruit is soaked in water overnight to hydrate it and make it soft. Afterwards, it is subjected to pulping by mixing well with an agitator to create a homogeneous pulp of the fruit. This pulp is mixed with just enough demineralized water to make it a flowable and the juice is subjected to filtration as described above for the fresh juice.

The procedure continues by passing the juice through an ion exchange system whereby the desired molecules are retained by the system and the other contents of the juice are allowed to pass through. The ion exchange system comprises a column containing a strong cation exchange resin like Amberlite IRA 120, or equivalent. The column is then washed with demineralized water to remove all the undesired components. Finally, the column is eluted with an alcohol-acid solution and the pigment-containing components are recovered. The column elution can be accomplished with methanol, ethanol, isopropanol, or any other suitable alcohol containing hydrochloric acid or, preferably, an organic acid such as acetic acid, citric acid, tartaric acid or hydroxy citric acid. The eluate is concentrated under vacuum at 40° C. to obtain the pigment components as a semisolid or paste. This paste is maintained in a color-stabilized condition by adding one or more suitable antioxidant such as tocopherol, *Occimum sanctum* extract, or *Azadiracta indica* extract. Alternatively, or additionally, the color of the extract is maintained by aseptically packaging the extract under an inert or non-oxidative atmosphere such as nitrogen gas or helium gas, or by drawing a vacuum. Keeping the extract under a nitrogen atmosphere until the container is opened for use is preferred.

EXAMPLE 1

1 Kg of *Garcinia indica* fruits are cut into small pieces of 25 mm to 50 mm size and soaked in 2 liters of demineralized water at a temperature in the range of 15° C. to 60° C. for not less than 12 hours. The resulting mixture is then pulped using a conventional food mixer to produce a thick pulp. The pulp is mixed with an additional 2 liters of demineralized water. The resulting thinned pulp is then filtered to remove all suspended particles, yielding about five liters of clear solution. This solution is passed through a column containing 500 ml of Amberlite IRA™ 120 or Dowex™ 50 W×8 or Tulsion™ T-42 MP, or Tulsion™ T-72 MP. The eluates are monitored for color. When the color passes unabsorbed, the column operation is stopped, and the column is washed with 5 liters of demineralized water, until only clear, colorless water emerges from the column outlet. The contents of the column are then eluted with 2 liters of 8% methanolic hydrochloric acid. The eluent is collected and concentrated under vacuum (25-50 mm of mercury) at less than 40° C. (preferably between 20-35° C.) to provide about 8 g of concentrate having a thick or paste-like consistency. The concentrate is then stabilized by adding 50 to 80 mg of the extract of *Occimum sanctum* as an antioxidant to promote color retention by the concentrate.

EXAMPLE 2

The procedure of Example 1 is repeated except that instead of adding the antioxidant to the concentrate, the concentrate is placed in an aseptic package or container under nitrogen atmosphere to maintain stability of the color. Alternatively, instead of using a nitrogen atmosphere, another suitable inert or non-oxidative atmosphere is used, such as helium gas, or by drawing a vacuum.

EXAMPLE 3

The procedure of Example 1 is repeated except that after the antioxidant is mixed with the concentrate, the resulting mixture is aseptically packaged in a non-oxidizing atmosphere, as described in Example 2.

EXAMPLE 4

The procedure of Example 1 is repeated except the eluting solvent is isopropyl alcohol containing 5-8% hydrochloric acid instead of the methanol-HCl solution. The weight of concentrate obtained is about 9 gms.

EXAMPLE 5

The procedure of Example 1 is repeated except in this instance the column is eluted with ethanol containing 5-8% hydrochloric acid. The amount of resulting concentrate is about 7.5 gms.

EXAMPLE 6

The procedure of Example 1 is repeated except the eluting solvent is isopropyl alcohol containing 5-8% citric acid instead of the methanol-HCl solution. The weight of concentrate obtained is about 9 gms.

EXAMPLE 7

The procedure of Example 1 is repeated except in this instance the column is eluted with ethanol containing 5-8% tartaric acid. The amount of resulting concentrate is about 7.5 gms.

EXAMPLE 8

The procedure of Example 1 is repeated except in this instance the column is eluted with ethanol containing 5-8% hydroxy citric acid. The amount of resulting concentrate is about 7.5-9 gms.

EXAMPLE 9

The procedure of Example 1 is repeated except in this instance the column is eluted with ethanol containing 5-8% acetic acid. The amount of resulting concentrate is about 7.5-9 gms.

EXAMPLE 10

Stability of the Anthocyanin Composition

A solution containing 1 gm of a representative concentrate prepared as described in Example 1 is dissolved in 100 ml of demineralized water. The resulting clear solution has a bright red color and a pH of 2 to 3. When 10% citric acid or acetic acid is dissolved in this solution, the red color is stable when heated to 80° C. and held at that temperature for 15 minutes. When heated to 95° C. and held at that temperature for 15 minutes, the color remains mostly stable with minor degradation.

Although the extract of *Occimum sanctum* was employed in Example 1, one or more other suitable antioxidant such as tocophenol, *Azadiracta indica* extract or the like, may be added to the concentrate to improve retention of the red color in the *Garcinia* extract, and in red-colored aqueous solutions prepared from the stabilized extract. For example, *Occimum sanctum* leaves are ground and extracted with water and dried into a powder for use as a color stabilizing agent. The color concentrate, with or without an added color stabilizing agent is preferably kept stable under nitrogen atmosphere in aseptic packaging. This helps to minimize the degradation of the anthocyanin color due to oxidation enabled by heat, light and oxygen.

Analysis of the Anthocyanin Composition

Plants that contain anthocyanins also invariably contain flavanoids. The distribution of flavanoids is more wide spread among plants than that of anthocyanins. The extracts described above were found to contain hydroxycitric acid, citric acid, lactones of those acids and various polymers of flavanoids and catechin. Most of the tinctorial power of the extracts is due to the complexed anthocyanins.

Structural Analysis. The red concentrate prepared from the *Garcinia* fruit juice as described in Example 1 was subjected to molecular ion studies using high performance liquid chromatography (HPLC) and mass spectroscopy (MS). The anthocyanins were detected using HPLC. For detection of anthocyanidins, the sample was hydrolyzed and then analyzed by HPLC. The HPLC procedure included subjecting the sample to ion exchange chromatography, both quantitative and using reverse phase C-18 columns. The HPLC chromatogram is presented in FIG. 1, showing the anthocyanin elution profile with two major peaks at 9.200 and 9.786 min., which are believed to indicate cyanidin-3-glucoside and cyanidin-3-sambubioside, respectively. The HPLC results for a representative red-colored extract are summarized in Table 1. Hydrolysis of the sample showed that cyanidin was the only aglycon present.

TABLE 1

Summary of HPLC Analysis

| Percentage of Area | | | | | | | Total % |
|---|---|---|---|---|---|---|---|
| unknown | unknown | unknown | unknown | cyd-3-samb | cyd-3-glu | unknown | unknowns |
| 0.63 | 0.31 | 0.39 | 0.59 | 35.46 | 61.11 | 1.50 | 4.32 |

Figure 2:
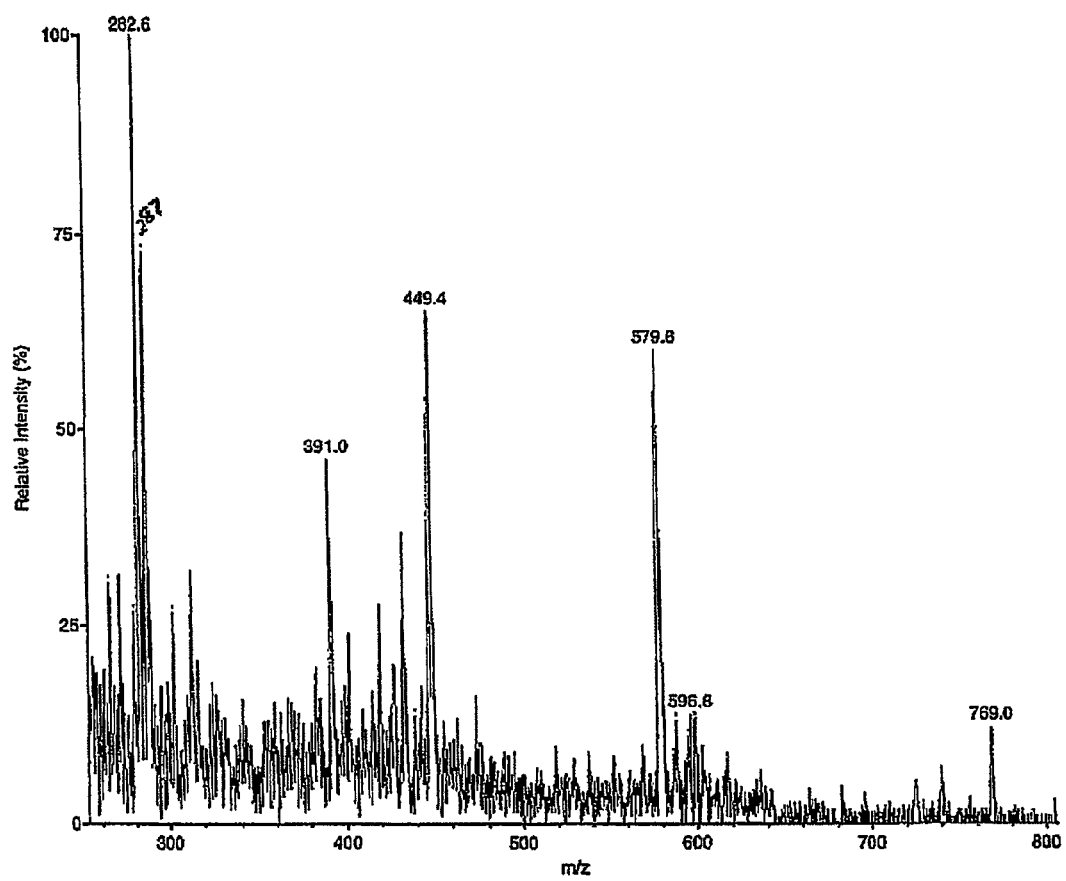
FIG. 2 is a mass spectroscopy spectrum of the representative sample of FIG. 1.

An identical sample was slightly purified and direct injected for anthocyanin molecular ion analysis by MS. The mass spectroscopy spectrum (FIG. 2) shows strong ion peaks at 449 (cyanidin-3-glucoside) and 287 (cyanidin). The strong ion peak at 580 is believed to be cyanidin-3-sambubioside, although the peak is one mass unit lower than the 581 expected for cyanidin-3-sambubioside. (The peak at 391 is a background peak due to an instrument contaminant.) The ions at 597 and 769 are unknown and do not match any common anthocyanins. Since the fraction subjected to mass spectroscopy analysis was not pure anthocyanins, the unknown chemical species are believed to be non-anthocyanin contaminants in the sample, for instance, phenolics. There were no ions present that would indicate the presence of aglycons other than cyanidin in the sample.

From these analyses it was concluded that the sample (prepared as described in Example 1) contains two major anthocyanin species that were identified as cyanidin-3-glucoside (approximately 61%) and most likely cyanidin-3-sambubioside (approximately 35%). The remaining approximately 3% of the red-colored extract is comprises five very minor anthocyanins of unknown composition.

From these studies it was determined that the red extract exists in two forms: cyanidin-3-glucoside, which showed peak at 449 (indicating cyanidin-3-glucoside) and at 287 (confirming cyanidin. The content of this compound is approximately 61% in the concentrated extract of Example 1. The other primary component of the extract was identified as cyanidin-3-sambubioside, and presented a peak at 581 in the MS spectrum. This compound makes up approximately 35% of the weight of the concentrate prepared as described in Example 1.

Antioxidant Properties of the Anthocyanin Composition

The representative anthocyanin composition prepared as described in Example 1 was tested in the following bioassays:

Autoxidation of Linoleic Acid in a Water-Alcohol System. This assay evaluated the inhibitory activity of the sample against lipid peroxidation (oxidation of fatty acids) caused by hydrogen peroxides.

Xanthine/Xanthine Oxidase Superoxide Scavenging System. This assay evaluated the scavenging activity of the sample on superoxide free-radical anions.

DPPH Radical Scavenging Assay. This assay evaluated the reducing activity of the sample that determines its antioxidant potential (AOP).

Tyrosinase Inhibitory Assay. This assay evaluated the antioxidant ability of the sample to inhibit the catalytic pathway of melanin pigment biosynthesis, thus resulting in skin whitening property. The assay results are given in Table 2.

TABLE 2

| No. | Sample Description | Extract | Superoxide Scavenging (%) | | DPPH Radical Scavenging (%) | | Tyrosinase Inhibitory Activity (%) | |
|---|---|---|---|---|---|---|---|---|
| 1. | Anthocyanin | $H_2O$ | 85.1 | H | 71.6 | H | 31.7 | L |

H=high; M=moderate; L=low; nt=not tested. The foregoing data suggest that the *Garcinia* extract will be valuable not only for its red colorant property, but also for its antioxidant properties which are likely to be active in vivo. The stabilized red colorant composition, prepared as described above, is suitable for use in a variety of applications, including food coloring, beverages, nutraceuticals, pharmaceuticals, toiletries, and the like, and as a natural antioxidant in such products.

Without further elaboration, it is believed that one skilled in the art can, using the description herein, utilize the present invention to its fullest extent. The foregoing embodiments are to be construed as illustrative, and not as constraining the remainder of the disclosure in any way whatsoever. While the preferred embodiments of the invention have been shown and described, modifications thereof can be made by one skilled in the art without departing from the spirit and teachings of the invention. Many variations and modifications of the invention disclosed herein are possible and are within the scope of the invention. Accordingly, the scope of protection is not limited by the description set out above, but is only limited by the claims which follow, that scope including all equivalents of the subject matter of the claims. The disclosures of all patents, patent applications and publications cited herein are hereby specifically incorporated herein by reference, to the extent that they provide materials, methods or other details supplementary to those set forth herein.

What is claimed is:

1. A method of making a red pigmented composition comprising:
    preparing an aqueous extract of *Garcinia indica* fruit comprising at least one red colorant;
    treating said extract with a cation exchange resin such that said at least one red colorant associates with said resin;
    eluting said at least one red colorant from said resin with an eluting solution comprising at least one alcohol and at least one acid to yield a red-colored eluate;
    collecting and concentrating said eluate to provide a concentrate.

2. The method of claim 1 wherein said at least one alcohol is selected from the group consisting of methanol, ethanol and isopropanol and said at least one acid is selected from the group consisting of hydrochloric acid, citric acid, acetic acid, tartaric acid and hydroxy citric acid.

3. The method of claim 1 comprising placing said concentrate in a non-oxidizing atmosphere in an aseptic container.

4. The method of claim 3 wherein said non-oxidizing atmosphere comprises a vacuum or a gas selected from the group consisting of nitrogen and helium.

5. The method of claim 1 wherein said concentrating comprises evaporating under vacuum at a temperature below 40° C.

6. The method of claim 5 wherein said vacuum is in the range of 25-50 mm mercury and/or said temperature is in the range of 20-35° C.

7. The method of claim 1 comprising washing said resin with water before said eluting.

8. The method of claim 1 comprising adding a color stabilizing agent to said concentrate.

9. The method of claim 8 wherein adding a color stabilizing agent comprises combining with said concentrate at least one antioxidant selected from the group consisting of tocopherol, aqueous extracts of *Occimum sanctum*, and aqueous extracts of *Azadiracta indica*.

10. A product comprising a color-stabilized red pigmented extract of *Garcinia indica* containing at least one anthocyanin compound wherein said extract is contained in aseptic packaging in a non-oxidizing atmosphere, and wherein said extract is prepared by the method of claim 3.

11. The product of claim 10 wherein said non-oxidizing atmosphere comprises nitrogen gas.

12. The product of claim 10 wherein said extract further includes at least one color stabilizing agent selected from the group consisting of tocopherol, aqueous extracts of *Occimwn sanctum*, and aqueous extracts of *Azadiraaa indica*.

13. The eembinatien-product of claim 10 wherein said extract is in the form of a concentrate.

14. The product of claim 10 wherein said extract is in the form of an aqueous solution.

15. The product of claim 10 wherein said product a food coloring, beverage, nutraceutical, pharmaceutical or toiletry.

16. The product of claim 10 wherein said extract comprises cyanidin-3-glucoside and cyanidin-3-sambubioside.

17. The product of claim 16 wherein said extract comprises about 61 wt % cyanidin-3-glucoside and about 35 wt % eyanidin-3-sambubioside.

18. The product of claim 10 wherein said extract is present in a product selected from the group consisting of food colorings, foods, beverages, nutraceuticals, pharmaceuticals and toiletries.

19. A method of tinting a food, beverage, nutraceutical, pharmaceutical or toiletry product comprising:
  obtaining a color-stabilized red pigmented extract of *Garcinia indica*, including at least one anthocyanin compound, contained in aseptic packaging in a non-oxidizing atmosphere, wherein said extract is prepared by the method of claim 3;
  and delivering from said packaging a sufficient amount of the color stabilized red pigmented extract to said food, beverage, nutraceutical, pharmaceutical or toiletry product to impart a red color.

* * * * *